United States Patent
Haibach et al.

(10) Patent No.: US 12,097,326 B2
(45) Date of Patent: Sep. 24, 2024

(54) PATIENT INTERFACE HAVING A RESTRICTOR ELEMENT FOR VARYING FLOW RESISTANCE THROUGH AN EXHALATION PORT THEREOF

(71) Applicant: KONINKLIJKE PHILIPS N.V., Eindhoven (NL)

(72) Inventors: Richard Thomas Haibach, Verona, PA (US); Lauren Patricia Chodkowski, Pittsburgh, PA (US); Anthony Vincent Startare, Belle Vernon, PA (US); Michael Joseph Mussallem, Pittsburgh, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 965 days.

(21) Appl. No.: 17/110,356

(22) Filed: Dec. 3, 2020

(65) Prior Publication Data
US 2021/0170131 A1    Jun. 10, 2021

Related U.S. Application Data

(60) Provisional application No. 62/945,583, filed on Dec. 9, 2019.

(51) Int. Cl.
*A61M 16/06* (2006.01)

(52) U.S. Cl.
CPC . *A61M 16/0666* (2013.01); *A61M 2205/3334* (2013.01)

(58) Field of Classification Search
CPC ..... A61D 7/00; A61M 16/0057; A61M 16/06; A61M 16/0633; A61M 16/0638; A61M 16/0644; A61M 16/065; A61M 16/0683; A61M 16/0816; A61M 16/0825; A61M 16/0875; A61M 16/22; A61M 2202/0085; A61M 2202/0225; A61M 2205/42; A61M 2205/7536; A62B 18/02; A62B 18/10; B23P 11/02; Y10T 29/49872
See application file for complete search history.

(56) References Cited

U.S. PATENT DOCUMENTS

| | | | |
|---|---|---|---|
| 6,581,594 B1 * | 6/2003 | Drew | A61M 16/0633 128/207.12 |
| 8,061,357 B2 | 11/2011 | Doshi et al. | |
| 2003/0079751 A1 * | 5/2003 | Kwok | B23P 11/02 128/206.15 |
| 2011/0203598 A1 | 8/2011 | Favet et al. | |
| 2016/0361067 A9 | 12/2016 | Cline et al. | |

* cited by examiner

*Primary Examiner* — Annette Dixon
(74) *Attorney, Agent, or Firm* — Michael W. Haas

(57) ABSTRACT

A patient interface for use in delivering a flow of a breathing gas to an airway of a patient includes a body that defines a cavity therein that is structured to receive the flow of breathing gas. A first aperture defined in the body is positioned and structured to communicate the flow of breathing gas from the cavity to an airway of the patient. A second aperture defined in the body is sized and configured to provide a pathway between the cavity and an ambient environment in which the body is disposed. The patient interface further includes a restrictor element that is selectively coupled to the body. The restrictor element includes a blocking portion that obstructs at least a portion of the second aperture.

12 Claims, 7 Drawing Sheets

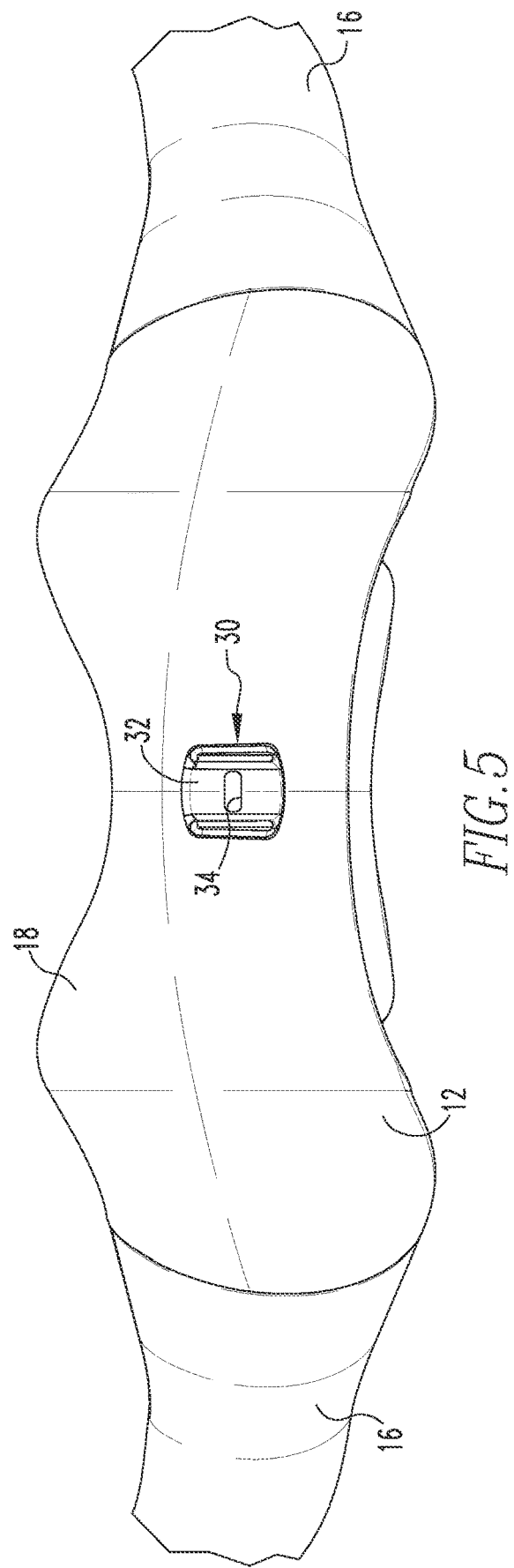

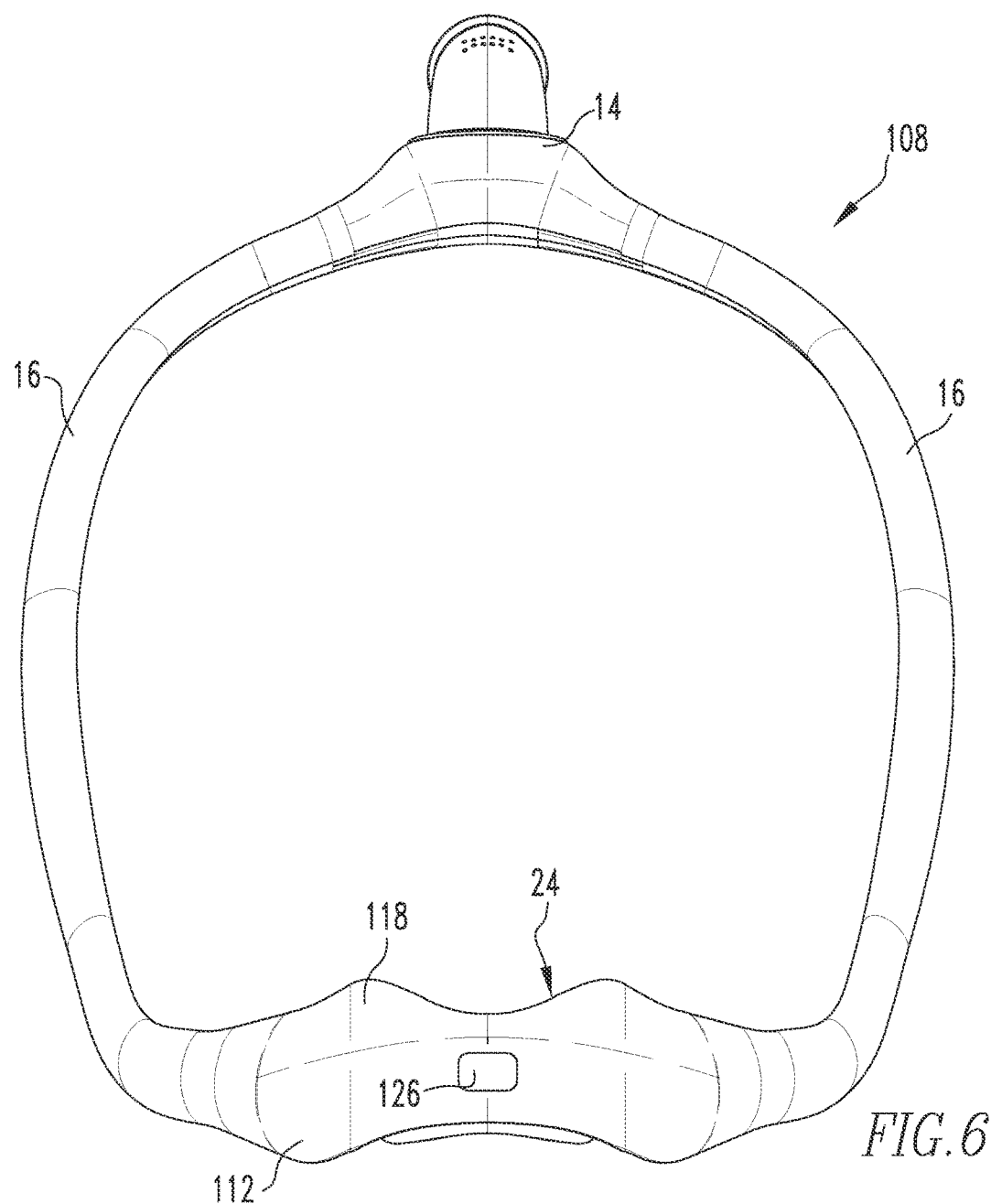
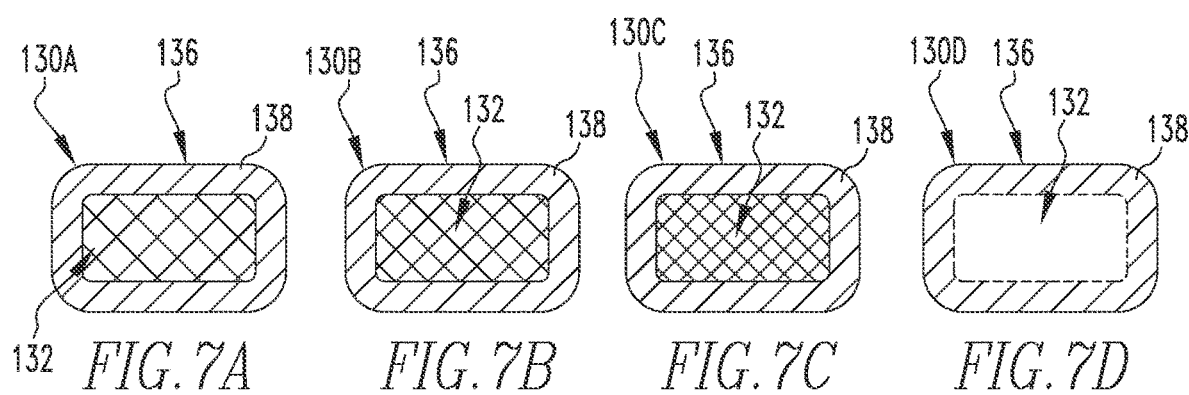
FIG. 6
FIG. 7A  FIG. 7B  FIG. 7C  FIG. 7D

PATIENT INTERFACE HAVING A RESTRICTOR ELEMENT FOR VARYING FLOW RESISTANCE THROUGH AN EXHALATION PORT THEREOF

CROSS-REFERENCE TO RELATED APPLICATIONS

This patent application claims the priority benefit under 35 U.S.C. § 119(e) of U.S. Provisional Application No. 62/945,583, filed on Dec. 9, 2019, the contents of which are herein incorporated by reference.

BACKGROUND OF THE INVENTION

1. Field of the Invention

The present invention pertains to patient interfaces for use in delivering a flow of a breathing gas to an airway of a patient. More particularly, the present invention pertains to patient interfaces having a restrictor element for tailoring the resistance of an exhaust port thereof. The present invention further pertains to kits for use in selectively tailoring the flow resistance of an exhaust port in a patient interface for use in delivering a flow of a breathing gas to an airway of a patient.

2. Description of the Related Art

Many individuals suffer from disordered breathing during sleep. Sleep apnea is a common example of such sleep disordered breathing suffered by millions of people throughout the world. One type of sleep apnea is obstructive sleep apnea (OSA), which is a condition in which sleep is repeatedly interrupted by an inability to breathe due to an obstruction of the airway; typically the upper airway or pharyngeal area. Obstruction of the airway is generally believed to be due, at least in part, to a general relaxation of the muscles which stabilize the upper airway segment, thereby allowing the tissues to collapse the airway. Another type of sleep apnea syndrome is a central apnea, which is a cessation of respiration due to the absence of respiratory signals from the brain's respiratory center. An apnea condition, whether obstructive, central, or mixed, which is a combination of obstructive and central, is defined as the complete or near cessation of breathing, for example a 90% or greater reduction in peak respiratory airflow.

Those afflicted with sleep apnea experience sleep fragmentation and complete or nearly complete cessation of ventilation intermittently during sleep with potentially severe degrees of oxyhemoglobin desaturation. These symptoms may be translated clinically into extreme daytime sleepiness, cardiac arrhythmias, pulmonary-artery hypertension, congestive heart failure and/or cognitive dysfunction. Other consequences of sleep apnea include right ventricular dysfunction, carbon dioxide retention during wakefulness, as well as during sleep, and continuous reduced arterial oxygen tension. Sleep apnea sufferers may be at risk for excessive mortality from these factors as well as by an elevated risk for accidents while driving and/or operating potentially dangerous equipment.

Even if a patient does not suffer from a complete or nearly complete obstruction of the airway, it is also known that adverse effects, such as arousals from sleep, can occur where there is only a partial obstruction of the airway. Partial obstruction of the airway typically results in shallow breathing referred to as a hypopnea. A hypopnea is typically defined as a 50% or greater reduction in the peak respiratory airflow. Other types of sleep disordered breathing include, without limitation, upper airway resistance syndrome (UARS) and vibration of the airway, such as vibration of the pharyngeal wall, commonly referred to as snoring.

It is well known to treat sleep disordered breathing by applying a continuous positive air pressure (CPAP) to the patient's airway. This positive pressure effectively "splints" the airway, thereby maintaining an open passage to the lungs. It is also known to provide a positive pressure therapy in which the pressure of gas delivered to the patient varies with the patient's breathing cycle, or varies with the patient's breathing effort, to increase the comfort to the patient. This pressure support technique is referred to as bi-level pressure support, in which the inspiratory positive airway pressure (IPAP) delivered to the patient is higher than the expiratory positive airway pressure (EPAP). It is further known to provide a positive pressure therapy in which the pressure is automatically adjusted based on the detected conditions of the patient, such as whether the patient is experiencing an apnea and/or hypopnea. This pressure support technique is referred to as an auto-titration type of pressure support, because the pressure support device seeks to provide a pressure to the patient that is only as high as necessary to treat the disordered breathing.

Pressure support therapies as just described involve the placement of a patient interface device including a mask component having a soft, flexible sealing cushion on the face of the patient. The mask component may be, without limitation, a nasal mask that covers the patient's nose, a nasal/oral mask that covers the patient's nose and mouth, or a full face mask that covers the patient's face. Such patient interface devices may also employ other patient contacting components, such as forehead supports, cheek pads and chin pads. The patient interface device is typically secured to the patient's head by a headgear component. The patient interface device is connected to a gas delivery tube or conduit and interfaces the pressure support device with the airway of the patient, so that a flow of breathing gas can be delivered from the pressure/flow generating device to the airway of the patient.

Humidifiers are frequently provided between or integral with a PAP machine and the user interface in order to humidify the otherwise relatively-dry compressed air generated by the PAP machine. The most conventional type of humidification used in homecare ventilation is a passover arrangement. In such arrangement, air from the CPAP machine flows into a water chamber and over an area of water before exiting the humidifier and passing on to the patient. This carries the moisture via a patient circuit (i.e., tubing and mask) to the patient. The water can be at room temperature or at an elevated temperature. The elevated temperate approach is more popular because it delivers more water in the air due to the fact that it is heated. The water for this type of humidifier is commonly heated using a resistive heater and has multiple set points for comfort.

Small travel CPAP devices typically do not have built-in or stand-alone humidifiers and in-line humidifiers (i.e., HMEs) are very large compared to the small form factors of many modern CPAP masks. Hence, it would be desirable to provide the benefits of a humidifier in small travel CPAP or in other instances where a conventional humidifier arrangement is unavailable or undesirable.

SUMMARY OF THE INVENTION

Embodiments of the present invention provide a patient receiving treatment via a patient interface with adequate humidity without the use of a large tank-style humidifier or an obtrusive HME. As one aspect of the invention, a patient interface for use in delivering a flow of a breathing gas to an airway of a patient is provided. The patient interface comprises: a body defining a cavity therein that is structured to receive the flow of breathing gas; a first aperture defined in the body, the first aperture being positioned and structured to communicate the flow of breathing gas from the cavity to an airway of the patient; a second aperture defined in the body, the second aperture being sized and configured to provide a pathway between the cavity and an ambient environment in which the body is disposed; and a restrictor element selectively coupled to the body, the restrictor element comprising a blocking portion that obstructs at least a portion of the second aperture.

The blocking portion may include an opening defined therethrough having a smaller cross-sectional area than the second aperture of the body such that when the blocking portion is disposed over the second aperture the cross-sectional area of the second aperture is limited to that of the opening.

The blocking portion may comprise a membrane of a predetermined porosity.

The restrictor element may further include a securement arrangement securing the restrictor element to the body such that the blocking portion covers the second aperture.

The securement arrangement may comprise a first prong and a second prong that each extend from the blocking portion and are both disposed at least partially in the second aperture and engage the body in a manner that secures the blocking portion in place covering the second aperture.

Each of the first and second prongs may engage the body in a manner that provides a snap-fit or a friction-fit between the restrictor element and the body.

The securement arrangement may comprise an adhesive that secures the blocking portion in place covering the second aperture.

The securement arrangement may comprise a flange that engages the body in a manner that secures the blocking portion in place covering the second aperture.

As another aspect of the invention a kit for use in selectively tailoring the flow resistance of an exhaust port in a patient interface for use in delivering a flow of a breathing gas to an airway of a patient is provided. The kit comprises a plurality of restrictor elements, each restrictor element comprising: a blocking portion structured to obstruct at least a portion of the exhaust port; and a securement arrangement structured to selectively couple the restrictor element to the body such that the blocking portion covers the exhaust port.

The blocking portion may include an opening defined therethrough having a smaller cross-sectional area than the exhaust port such that when the blocking portion is disposed over the exhaust port the cross-sectional area of the exhaust port is limited to that of the opening.

The opening of one of the restrictor elements may have a first cross-sectional area, and the opening of another one of the restrictor elements may have a second cross-sectional area different that the first cross-sectional area.

The blocking portion may comprise a membrane of a predetermined porosity.

The membrane of one of the restrictor elements may have a first porosity, and the membrane of another one of the restrictor elements may have a second porosity different than the first porosity.

The securement arrangement may comprise a structure adapted to selectively couple the restrictor element to the body via one of a snap-fit or a friction-fit.

The securement arrangement may comprise an adhesive.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

BRIEF DESCRIPTION OF THE DRAWINGS

FIG. 5 is a front elevation view of a portion of the mask of FIGS. 1 and 2 showing the restrictor elements of FIGS. 4A and 4B installed on the patient interface thereof;

FIG. 6 is a front elevation view of another mask in accordance with another example embodiment of the present invention;

FIGS. 7A-7D are example restrictor elements in accordance with example embodiments of the present invention for use with the patient interface of the mask of FIG. 6;

DETAILED DESCRIPTION OF EXEMPLARY EMBODIMENTS

Figure 1:
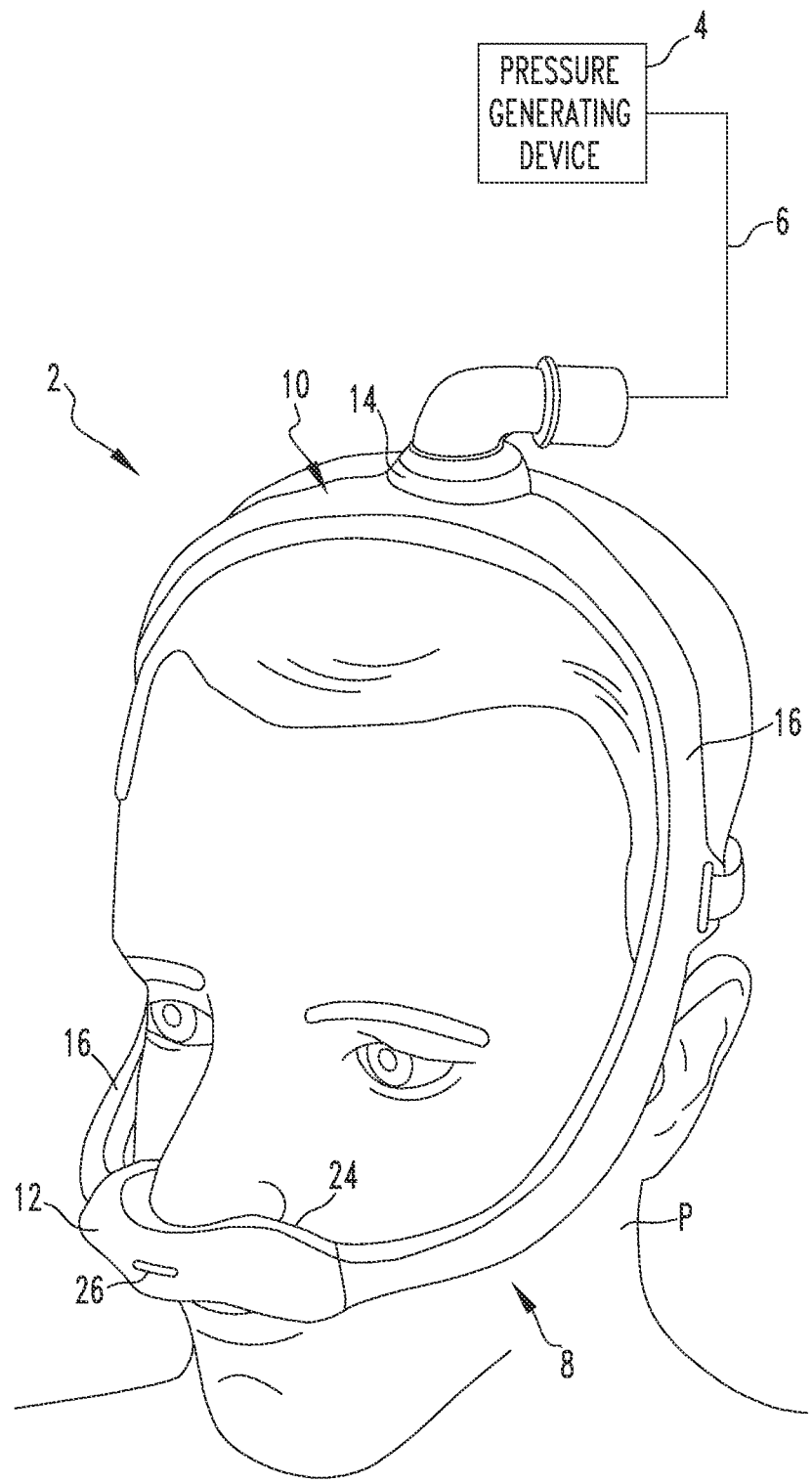
FIG. 1 is a partially schematic depiction of a respiratory interface system for use in providing a flow of positive pressure breathing gas to the airway of a patient in accordance with one example embodiment of the present invention, shown with a mask thereof disposed on the head of a patient.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

As used herein, the statement that two or more parts or components "engage" one another shall means that the parts exert a force against one another either directly or through one or more intermediate parts or components. As used herein, the word "unitary" means a component is created as a single piece or unit. That is, a component that includes pieces that are created separately and then coupled together as a unit is not a "unitary" component or body. As used herein, the term "number" shall mean one or an integer greater than one (i.e., a plurality).

As used herein, a "coupling assembly" includes two or more couplings or coupling components. The components of a coupling or coupling assembly are generally not part of the same element or other component. As such the components of a "coupling assembly" may not be described at the same time in the following description.

As used herein, a "coupling" is one element of a coupling assembly. That is, a coupling assembly includes at least two components, or coupling components, that are structured to be coupled together. It is understood that the elements of a coupling assembly are compatible with each other. For example, in a coupling assembly, if one coupling element is a snap socket, the other coupling element is a snap plug.

As used herein, "correspond" indicates that two structural components are sized and shaped to be similar to each other and may be coupled with a minimum amount of friction. Thus, an opening which "corresponds" to a member is sized slightly larger than the member so that the member may pass through the opening with a minimum amount of friction. This definition is modified if the two components are said to fit "snugly" together or "snuggly correspond." In that situation, the difference between the size of the components is even smaller whereby the amount of friction increases. If the element defining the opening and/or the component inserted into the opening is/are made from a deformable or compressible material, the opening may even be slightly smaller than the component being inserted into the opening. This definition is further modified if the two components are said to "substantially correspond." "Substantially correspond" means that the size of the opening is very close to the size of the element inserted therein. That is, not so close as to cause substantial friction, as with a snug fit, but with more contact and friction than a "corresponding fit," i.e. a "slightly larger" fit.

A respiratory interface system 2 adapted to provide a regimen of respiratory therapy to a patient P according to one exemplary embodiment of the present invention is shown in FIG. 1. Respiratory interface system 2 includes a pressure generating device 4 (shown schematically), and a delivery conduit 6 (shown schematically) fluidly coupled to a mask 8. Pressure generating device 4 is structured to generate a flow of positive pressure breathing gas and may include, without limitation, ventilators, constant pressure support devices (such as a continuous positive airway pressure device, or CPAP device), variable pressure devices (e.g., BiPAP®, Bi-Flex®, or C-Flex™ devices manufactured and distributed by Philips Respironics of Murrysville, PA), and auto-titration pressure support devices. Delivery conduit 6 is structured to communicate the flow of breathing gas from pressure generating device 4 to mask 8, and mask 8 is structured to further communicate the flow of breathing gas received from conduit 6 to an airway of patient P. Delivery conduit 6 and mask 8 are often collectively referred to as a patient circuit.

Figure 2:
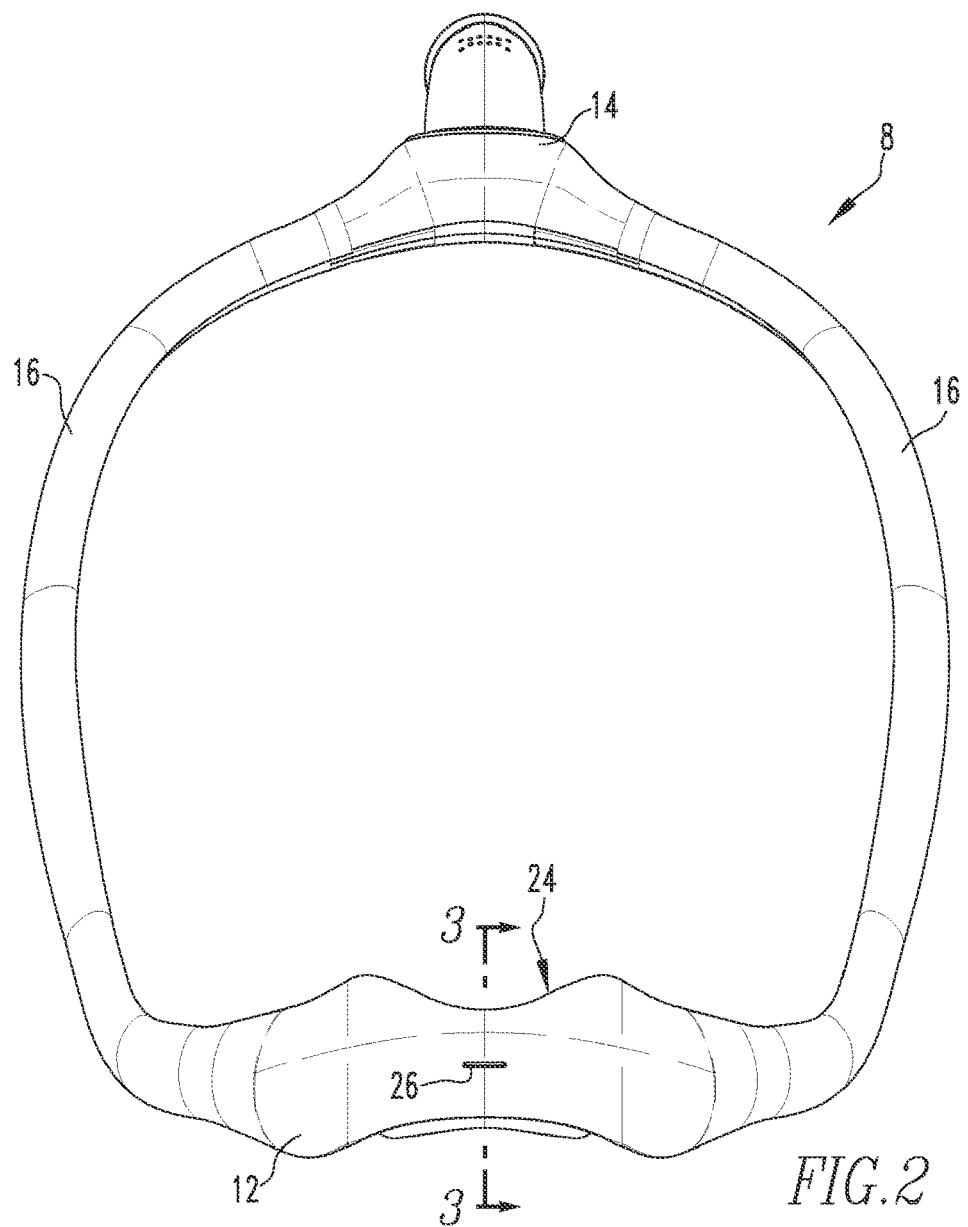
FIG. 2 is a front elevation view of the mask of FIG. 1.

Continuing to refer to FIG. 1, as well as to FIG. 2, mask 8 includes a tubing assembly 10 and a patient interface 12 fluidly coupled to tubing assembly 10. Tubing assembly 10 includes a manifold portion 14 structured to receive the flow of positive pressure breathing gas from delivery conduit 6, a number (two are shown in the example of FIGS. 1 and 2) of tubular portions 16 which each extend from manifold portion 14 to a distal end (not numbered) which is selectively coupled to patient interface 12. It is to be appreciated that other arrangements aside from tubing assembly 10 may be employed in mask 8 to provide the flow of positive pressure breathing gas produced by pressure generating device 4 to patient interface 12 without varying from the scope of the present invention.

Figure 3:
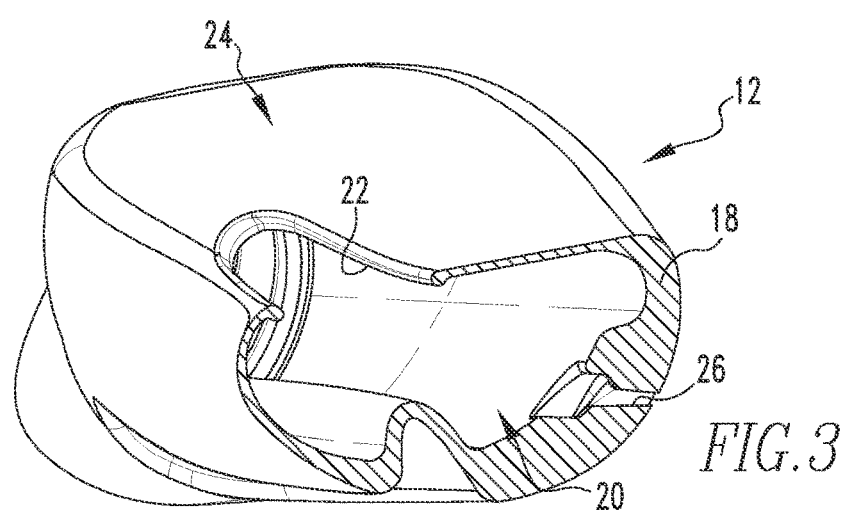
FIG. 3 is a section elevation view of the patient interface of the mask of FIG. 2 taken along line 3-3 of FIG. 2.

Referring now to FIG. 3, in addition to FIGS. 1 and 2, patient interface 12 includes a body 18 that defines a cavity 20 therein that is structured to receive (e.g., via tubing assembly 10) the flow of breathing produced by pressure generating device 4. In the one example shown in FIGS. 1-3, body 18 is made of a soft, flexible material, such as, without limitation, silicone, an appropriately soft thermoplastic elastomer, a closed-cell foam, or any other suitable material or combination of such materials, however, it is to be appreciated that body 18 may be formed from one or more other suitable materials without varying from the scope of the present invention.

Patient interface 12 further includes a first aperture 22 defined therein that is positioned and structured to communicate the flow of breathing gas from cavity 20 to the airway of the patient and a sealing element 24 disposed thereabout first aperture 22 which is structured to sealingly engage about one or more of the nares and/or mouth of patient P. In the example embodiment illustrated in FIGS. 1-3, sealing element 24 is formed as an integral portion of body 18, and thus is made of a soft, flexible material, such as, without limitation, silicone, an appropriately soft thermoplastic elastomer, a closed-cell foam, or any other suitable material or combination of such materials. It is to be appreciated, however, that sealing element 24 made be formed as a separate element and may take the form of any type of patient sealing element, such as a nasal/oral mask, a nasal pillow or a full face mask, which facilitates the delivery of the flow of breathing gas to the airway of a patient, without varying from the scope of the present invention.

Patient interface 12 further includes a second aperture 26 defined in body 18 that is sized and configured to provide a pathway between cavity 20 and an ambient environment in which body 18 is disposed. When patient interface 12 is positioned on the face of patient P, second aperture 26 functions as an exhalation port for venting gases exhaled by the patient from cavity 20 to the ambient environment in which patient P is positioned Embodiments of the present invention selectively increase the humidity of the air within cavity 20 by restricting the escape of gases exhaled by the patient through second aperture 26. As the gases exhaled by a patient are of a higher humidity than the flow of breathing gas produced by pressure generating device 4, restricting the escape of such exhaled gases effectively increases the humidity of the air within cavity 20 which is inhaled by the patient. In order to selectively restrict the escape of exhaled gases through second aperture 26, a restrictor element 30, such as the one example shown in FIGS. 4A and 4B, that reduces the size of second aperture 26 may be coupled to body 18. Restrictor element 30 includes a blocking portion 32 that obstructs at least a portion of second aperture 26 of body 18 when restrictor element 30 is coupled to body 18, such as shown in FIG. 5.

Figure 4A:
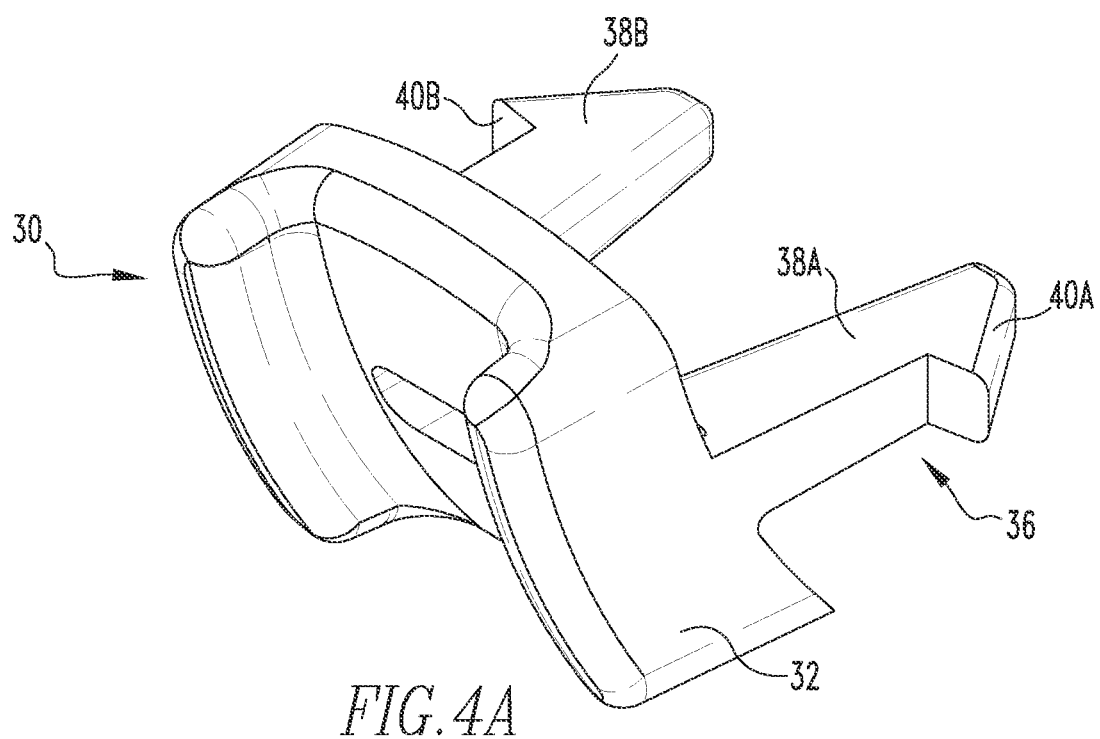
FIG. 4A is a perspective view of a restrictor element in accordance with one example embodiment of the present invention for use with the mask of FIGS. 1 and 2.
Figure 4B:
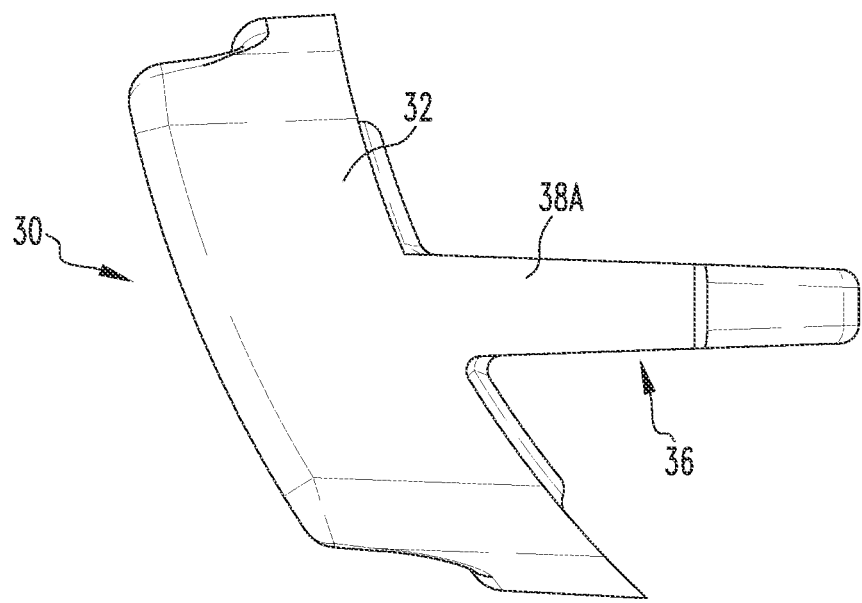
FIG. 4B is a side elevation view of the restrictor element of FIG. 4A.

In the example shown in FIGS. 4A and 4B, blocking portion 32 includes an opening 34 defined therethrough that has a smaller cross-sectional area than second aperture 26 of body 18 such that when blocking portion 32 is disposed over second aperture 26 the cross-sectional area of second aperture is limited to that of opening 34. Restrictor element 30 further includes a securement arrangement 36 for securing restrictor element 30 to body 18 such that blocking portion 32 covers second aperture 26 such as shown in FIG. 5. In the example shown in FIGS. 4A and 4B, securement arrangement 36 includes a first prong 38A and a second prong 38B that each extend from blocking portion 32 and are both sized and configured to be disposed at least partially in second aperture 26 and engage body 18 in a manner that secures blocking portion 32 in place covering second aperture 26. First and second prongs 38A and 38B may each include a flared portion 40A and 40B that engage body 18 providing a snap-fit between restrictor element 30 and body 18. In another example embodiment, first and second prongs 38A and 38B engage body 18 providing a friction fit between restrictor element 30 and body 18.

Another mask 108 in accordance with another example embodiment of the present invention is shown in FIG. 6. Mask 108 is of similar arrangement as mask 8 previously discussed in regard to FIGS. 1 and 2 and as such include tubing assembly 10 such as previously discussed. Mask 108 further includes a patient interface 112, similar to patient interface 12 previously discussed, that is fluidly coupled to tubing assembly 10. Patient interface 112 differs from patient interface 12 (previously discussed) in that patient interface 112 includes a second aperture 126 of a larger size (i.e., greater cross-sectional area) than second aperture 26 of patient interface 12. Such difference in sizing is due to the fact that second aperture 126 is sized and configured to be used only in conjunction with a restrictor element 130 (e.g., without limitation, such as shown in FIGS. 7A-7D, as well as FIGS. 9A and 9B) and not without (in contrast patient interface 12 is designed to be used without restrictor element 30, hence restrictor element functions generally as a retro-fit arrangement).

Figure 8A:
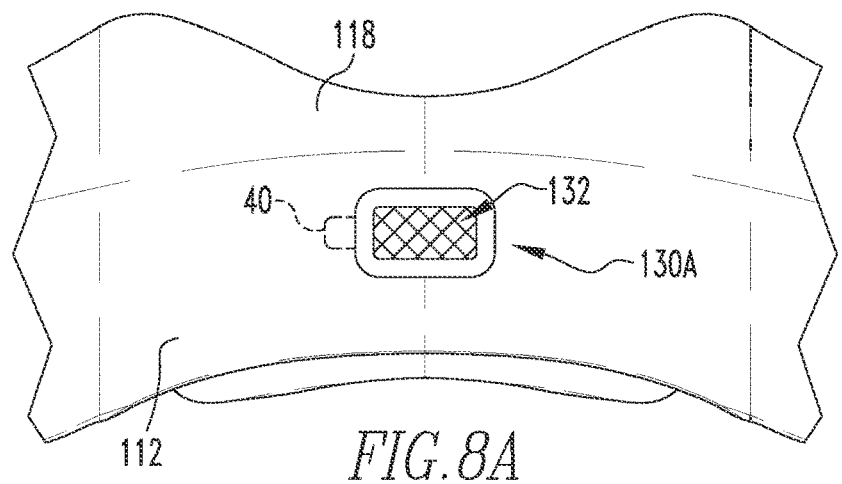
FIGS. 8A-8C, respectively, are detail views of the patient interface portion of the mask of FIG. 6 shown with the restrictor elements of FIGS. 7A-7C positioned thereon.
Figure 8B:
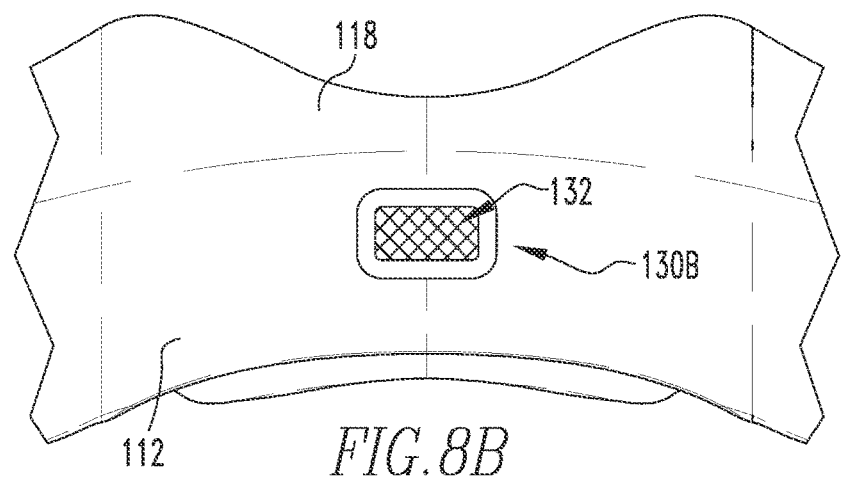
Figure 8C:
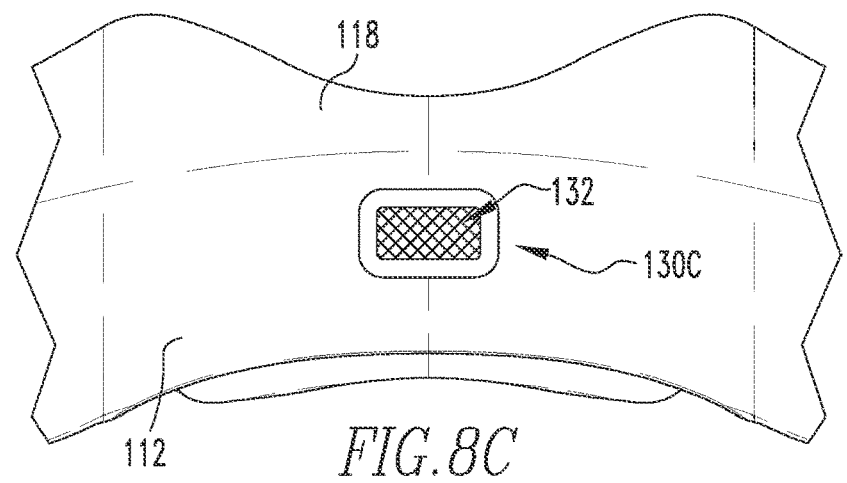

Referring now to FIGS. 7A-7D and 8A-8C, some restrictor elements 130A-130D in accordance with several example embodiments of the present invention for use with patient interface 112 are shown (partially schematically). Similar to restrictor element 30 previously discussed, each restrictor element 130A-130D includes a blocking portion 132 and a securement arrangement 136 for securing blocking portion 132 to body 118 of patient interface 112 such that blocking portion 132 covers second aperture 126 (such as shown in FIGS. 8A-8C).

Unlike the mechanical arrangement (i.e., prongs 38A and 38B) of securement arrangement 36 utilized in restrictor element 30, securement arrangements 136 of each of restrictor elements 130A-130D utilize an adhesive 138 (shown single-hatched in FIGS. 7A-7D for exemplary purposes) suitable for bonding to silicone. In the examples shown in FIGS. 7A-7D, adhesive 138 is disposed completely around blocking portion 132, however, it is to be appreciated that adhesive 138 could be otherwise suitably positioned without varying from the scope of the present invention.

Unlike restrictor element 30 that utilized smaller sized opening 34 to restrict flow through second aperture 26, restrictor elements 130A-130C utilize membranes (shown cross-hatched in FIGS. 7A-7D and 8A-8C) of different porosity as blocking portion 132 in order to provide different resistance to airflow therethrough. Hence, the flow of air through second apertures 126 of patient interface 112 may be selectively varied by adhering different ones of restrictor elements 130A-130D to body 118 with blocking portion 132 thereof covering second aperture 126. For example, such potential range of flow may vary from a very porous blocking portion 132, such as shown in restrictor element 130A, to a not porous (i.e., solid) blocking portion 132, such as shown in restrictor element 130D.

Restrictor elements 130A-130D may be formed by selectively depositing an adhesive on a mesh, film, fabric or other porous or non-porous sheet. From this sheet, restrictor element "stickers" can be cut with a laser, die, knife, or any method of cutting. For partially restrictive embodiments, the adhesive should not cover some portion of the sheet, allowing flow through the structure, but restricted compared to an open exhalation. The stickers may include a release tab, such as tab 40 shown in dashed line in FIG. 8A, without adhesive to aid in removal. The stickers may be provided on a sheet of release liner, in a multi-pack, or any other suitable "kit" form. The restrictor elements 130A-130D may be disposable or re-usable.

Figure 9A:
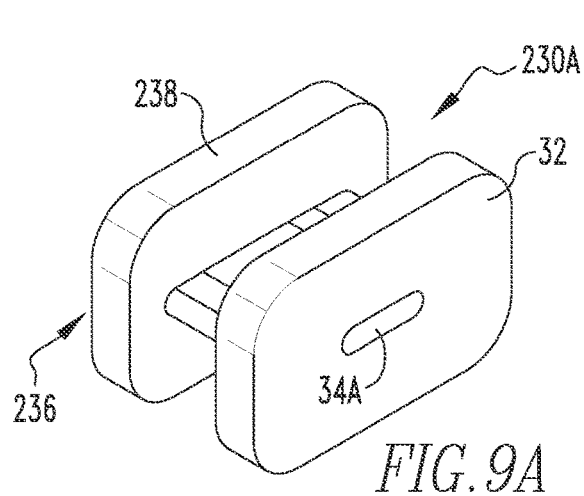
FIGS. 9A and 9B are further example restrictor elements in accordance with example embodiments of the present invention for use with the patient interface of the mask of FIG. 6.
Figure 9B:
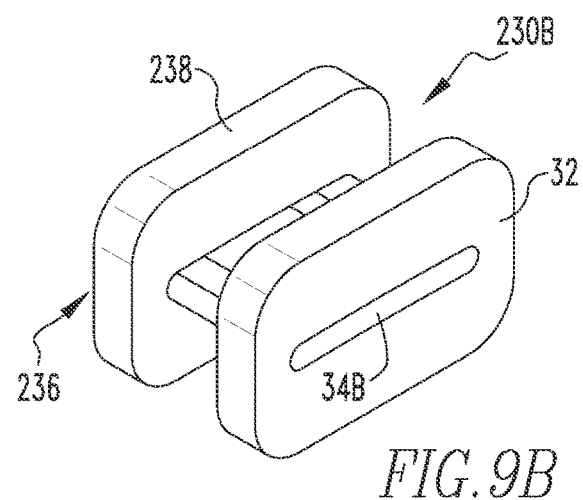
Figure 10A:
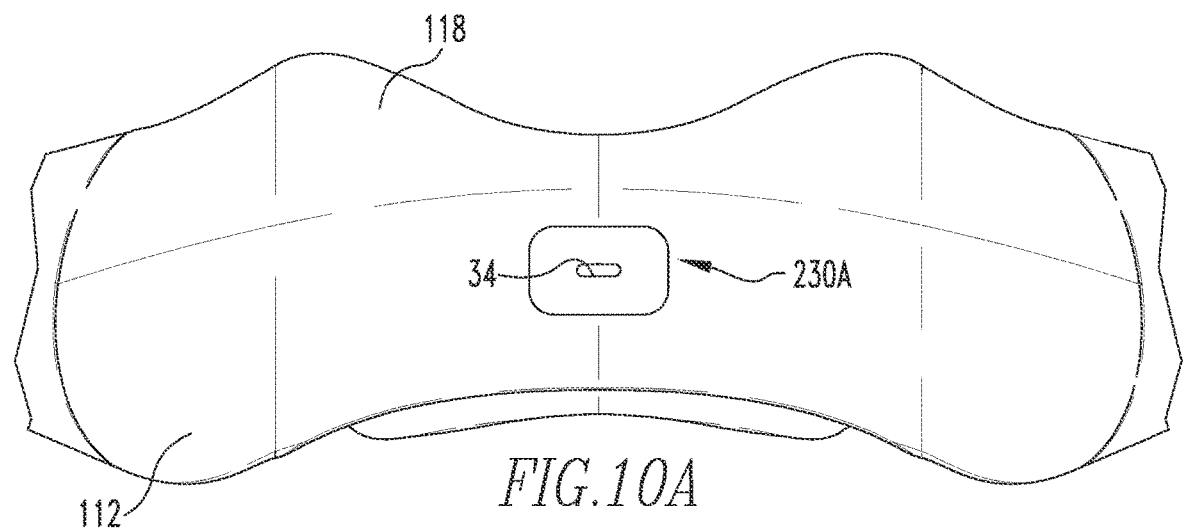
FIGS. 10A and 10B respectively, are detail views of the patient interface portion of the mask of FIG. 6 shown with the restrictor elements of FIGS. 9A and 9B positioned thereon.
Figure 10B:
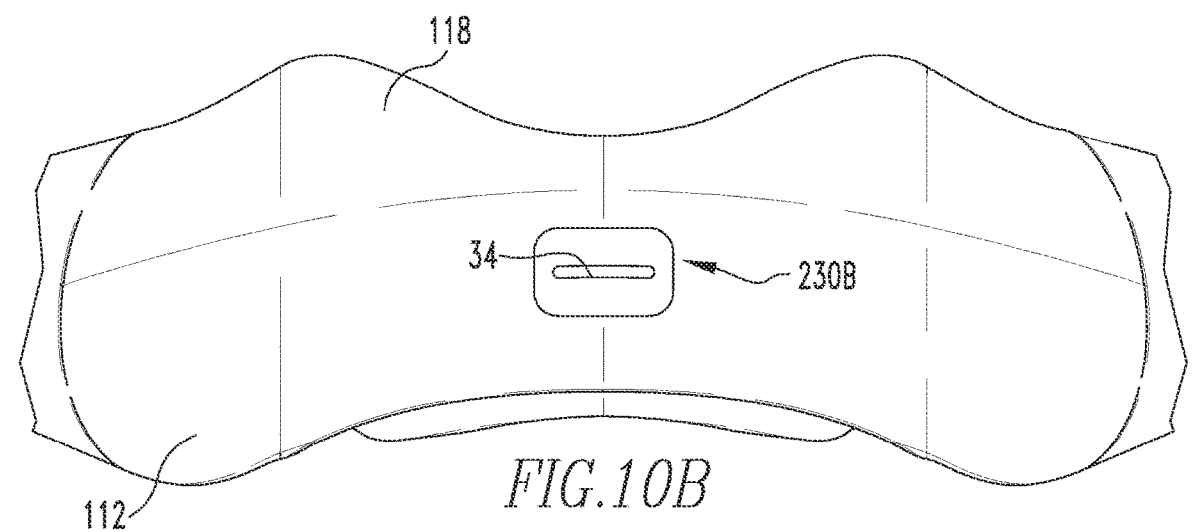

FIGS. 9A and 9B show further restrictor elements 230A and 230B in accordance with other example embodiments of the present invention that may be employed with patient interface 112. Restrictor elements 230A and 230B function similarly to restrictor element 30 previously discussed in regard to FIGS. 1-5. Accordingly, each restrictor element 230A and 230B includes a blocking portion 32 having an opening 34A, 34B and a securement arrangement 236 for securing each restrictor element 230A and 230B to body 118 such that blocking portion 32 thereof covers second aperture 126, such as shown in FIGS. 10A and 10B. In the example shown in FIGS. 9A and 9B, securement arrangement 236 includes a flange 238 that is sized and configured to engage body 118 (either within or adjacent to second aperture 126) in a manner that secures blocking portion 32 in place covering second aperture 126. Such engagement between flange 238 and body 118 may be structured to provide a snap-fit or a friction-fit between each restrictor element 230A or 230B and body 118. Similar to restrictor elements 130A-130D, restrictor elements 230A and 230B may be provided in a kit, allowing a user to select the resistance member desirable for their particular application.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment. Accordingly, it is to be appreciated that restrictor elements employing membranes may utilize mechanical securement arrangements without varying from the scope of the present invention. Likewise, restrictor elements utilizing different sized apertures may utilize adhesive securement arrangements without varying from the scope of the present invention.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

What is claimed is:

1. A patient interface for use in delivering a flow of a breathing gas to an airway of a patient, the patient interface comprising:
    a body defining a cavity therein that is structured to receive the flow of breathing gas;
    a first aperture defined in the body, the first aperture being positioned and structured to communicate the flow of breathing gas from the cavity to an airway of the patient;
    a second aperture defined in the body, the second aperture being sized and configured to provide a pathway between the cavity and an ambient environment in which the body is disposed; and
    a restrictor element selectively coupled to the body, the restrictor element comprising:
        a blocking portion that obstructs at least a portion of the second aperture; and
        a securement arrangement securing the restrictor element to the body such that the blocking portion covers the second aperture, the securement arrangement comprising a first prong and a second prong that each extend from the blocking portion into the second aperture such that the first prong and the second prong are both disposed at least partially in the second aperture and engage the body in a manner that secures the blocking portion in place covering the second aperture.

2. The patient interface of claim 1, wherein the blocking portion includes an opening defined therethrough having a smaller cross-sectional area than the second aperture of the body such that when the blocking portion is disposed over the second aperture the cross-sectional area of the second aperture is limited to that of the opening.

3. The patient interface of claim 1, wherein the blocking portion comprises a membrane of a predetermined porosity.

4. The patient interface of claim 1, wherein each of the first and second prongs engage the body in a manner that provides a snap-fit or a friction-fit between the restrictor element and the body.

5. The patient interface of claim 1, wherein the securement arrangement comprises an adhesive that secures the blocking portion in place covering the second aperture.

6. The patient interface of claim 1, wherein each of the first prong and the second prong includes a flared portion that engages the body in a manner that provides a snap-fit.

7. A kit for use in selectively tailoring the flow resistance of an exhaust port defined in a body of a patient interface for use in delivering a flow of a breathing gas to an airway of a patient, the kit comprising a plurality of restrictor elements, each restrictor element comprising:
    a blocking portion structured to obstruct at least a portion of the exhaust port; and
    a securement arrangement structured to selectively couple the restrictor element to the body such that the blocking portion covers the exhaust port, wherein the securement arrangement comprises a first prong and a second prong that are each extend from the blocking portion and are structured to extend into the second aperture such that the first prong and the second prong are both disposed at least partially in the second aperture and engage the body in a manner that secures the blocking portion in place covering the second aperture.

8. The kit of claim 7, wherein the blocking portion includes an opening defined therethrough having a smaller cross-sectional area than the exhaust port such that when the blocking portion is disposed over the exhaust port the cross-sectional area of the exhaust port is limited to that of the opening.

9. The kit of claim 8, wherein the opening of one of the restrictor elements has a first cross-sectional area, and wherein the opening of another one of the restrictor elements has a second cross-sectional area different that the first cross-sectional area.

10. The kit of claim 7, wherein the blocking portion comprises a membrane of a predetermined porosity.

11. The kit of claim 10, wherein the membrane of one of the restrictor elements has a first porosity, and wherein the membrane of another one of the restrictor elements has a second porosity different than the first porosity.

12. The kit of claim 7, wherein each of the first prong and the second prong of each restrictor element includes a flared portion that is structured to engage the body in a manner that provides a snap-fit.

* * * * *